(12) United States Patent
Kolb

(10) Patent No.: US 10,058,167 B2
(45) Date of Patent: Aug. 28, 2018

(54) ORAL CARE IMPLEMENT

(71) Applicant: Colgate-Palmolive Company, New York, NY (US)

(72) Inventor: Matthew Lee Kolb, Upper Black Eddy, PA (US)

(73) Assignee: Colgate-Palmolive Company, New York, NY (US)

( * ) Notice: Subject to any disclaimer, the term of this patent is extended or adjusted under 35 U.S.C. 154(b) by 130 days.

(21) Appl. No.: 15/106,514

(22) PCT Filed: Dec. 19, 2013

(86) PCT No.: PCT/US2013/076571
§ 371 (c)(1),
(2) Date: Jun. 20, 2016

(87) PCT Pub. No.: WO2015/094286
PCT Pub. Date: Jun. 25, 2015

(65) Prior Publication Data
US 2016/0331111 A1    Nov. 17, 2016

(51) Int. Cl.
*A46B 9/04*    (2006.01)
*A46B 11/00*    (2006.01)
(Continued)

(52) U.S. Cl.
CPC .......... *A46B 11/001* (2013.01); *A46B 5/0095* (2013.01); *A46B 5/021* (2013.01);
(Continued)

(58) Field of Classification Search
CPC ............................................. A46B 2200/1066
See application file for complete search history.

(56) References Cited

U.S. PATENT DOCUMENTS 6,526,991 B2 *  3/2003  Bodwalk ................ A45D 44/18
                                                                132/309
9,138,046 B2    9/2015  Jimenez et al.
(Continued)

FOREIGN PATENT DOCUMENTS

FR          2888736        1/2007
WO      WO2009087626       7/2009

OTHER PUBLICATIONS

Corresponding Search Report for PCT/US2013/076571 dated Sep. 8, 2014.

*Primary Examiner* — David Walczak
*Assistant Examiner* — Joshua Wiljanen

(57) ABSTRACT

Disclosed is an oral care implement, comprising: a body comprising a handle and a head at an end of the handle, the head having at least one oral care element extending therefrom; a cap movable relative to the body; a cavity in one of the body and the cap, the one of the body and the cap defining an opening of the cavity; and an applicator connected between the body and the cap and holding an oral care agent; wherein the cap is movable relative to the body between a first position, at which the cap is at a first distance from the body, and a second position, at which the cap is at a second distance from the body, wherein the second distance is greater than the first distance; wherein the applicator is located in the cavity and the other of the body and the cap blocks the opening when the cap is at the first position relative to the body; and wherein the applicator is in fluid communication with an exterior of the oral care implement when the cap is at the second position relative to the body.

20 Claims, 1 Drawing Sheet

(51) Int. Cl.
*A46B 5/00* (2006.01)
*A46B 5/02* (2006.01)
*A61C 17/22* (2006.01)

(52) U.S. Cl.
CPC ............ *A46B 9/04* (2013.01); *A46B 11/0041* (2013.01); *A46B 11/0086* (2013.01); *A61C 17/227* (2013.01); *A46B 2200/1066* (2013.01)

(56) References Cited

U.S. PATENT DOCUMENTS

2010/0067969 A1* 3/2010 Kang ................ A46B 11/0006
 401/118
2011/0318085 A1 12/2011 Alcocer

* cited by examiner

ORAL CARE IMPLEMENT

CROSS-REFERENCE TO RELATED PATENT APPLICATIONS

The present application is a U.S. national stage application under 35 U.S.C. § 371 of PCT Application No. PCT/US2013/076571, filed Dec. 19, 2013, the entirety of which is incorporated herein by reference.

BACKGROUND

The present invention relates to an oral care implement, such as a toothbrush.

It is known to provide an oral care implement, such as a toothbrush, with an applicator for applying an oral care agent, such as a tooth whitening agent, from the implement to an oral surface. For example, one known toothbrush comprises a first component having a head and a handle with a cavity in the handle, and a second component in the form of a dispenser containing an oral care agent and having an applicator via which the oral care agent may be applied from the dispenser to an oral surface. The dispenser is storable in the cavity when not in use, and fully removable from the cavity and detachable from the first component for use. Another known toothbrush has a head and a handle, with a single-use gel capsule comprising an oral care agent located within a field of tooth cleaning elements on the head. In use of the toothbrush, the gel capsule is burst as it is rubbed against a user's teeth, thereby applying the oral care agent to the teeth.

There is a need for an oral care implement with an applicator that is more convenient to use to apply an oral care agent to an oral surface. There also is a need for an oral care implement with a simpler applicator that is reusable for applying an oral care agent to an oral surface. There further is a need for an oral care implement that preserves an oral care agent prior to applying the oral care agent to an oral surface.

BRIEF SUMMARY

An embodiment of the present invention provides a first oral care implement, comprising: a body comprising a handle and a head at an end of the handle, the head having at least one oral care element extending therefrom; a cap movable relative to the body; a cavity in one of the body and the cap, the one of the body and the cap defining an opening of the cavity; and an applicator connected between the body and the cap and holding an oral care agent; wherein the cap is movable relative to the body between a first position, at which the cap is at a first distance from the body, and a second position, at which the cap is at a second distance from the body, wherein the second distance is greater than the first distance.

Optionally, the applicator is located in the cavity and the other of the body and the cap blocks the opening when the cap is at the first position relative to the body, and the applicator is in fluid communication with an exterior of the oral care implement when the cap is at the second position relative to the body.

Another embodiment of the present invention provides a second oral care implement, comprising: a body comprising a handle and a head at an end of the handle, the head having at least one oral care element extending therefrom; a cap movable relative to the body; a cavity in one of the body and the cap, the one of the body and the cap defining an opening of the cavity; and an applicator connected between the body and the cap and holding an oral care agent; wherein the cap is movable relative to the body between a first position, at which the applicator is located in the cavity and the other of the body and the cap blocks the opening, and a second position, at which the applicator is in fluid communication with an exterior of the oral care implement.

Optionally, in the second oral care implement, the cap is at a first distance from the body when the cap is at the first position relative to the body, the cap is at a second distance from the body when the cap is at the second position relative to the body, and the second distance is greater than the first distance.

Optionally, in either of the first and second oral care implements, the cavity is in the body. Further optionally, the cavity is in the handle. Still further optionally, the handle has a proximal end and a distal end, the head is at the distal end of the handle, and the opening is at the proximal end of the handle.

Optionally, in either of the first and second oral care implements, the cap is in contact with the body when the cap is at the first position relative to the body.

Optionally, in either of the first and second oral care implements, the cap is connected to the body only via the applicator when the cap is at the second position relative to the body.

Optionally, in either of the first and second oral care implements, the cap is non-unitary with the body.

Optionally, in either of the first and second oral care implements, the body and the cap comprise respective co-operable couplers for coupling the cap to the body when the cap is at the first position relative to the body. Further optionally, the respective co-operable couplers comprise a protrusion from one of the body and the cap and a depression in the other of the body and the cap.

Optionally, in either of the first and second oral care implements, the applicator is porous.

Optionally, in either of the first and second oral care implements, the applicator is non-detachable from one or both of the body and the cap.

Optionally, in either of the first and second oral care implements, the applicator is elastic.

Optionally, in either of the first and second oral care implements, the applicator is stretchable.

Optionally, in either of the first and second oral care implements, a first end of the applicator is at a fixed position relative to the body.

Optionally, in either of the first and second oral care implements, a second end of the applicator is at a fixed position relative to the cap.

Optionally, in either of the first and second oral care implements, a length of the applicator is dependent on a position of the cap relative to the body. Further optionally, the applicator has a first length when the cap is at the first position relative to the body, the applicator has a second length when the cap is at the second position relative to the body, and the second length is greater than the first length.

Optionally, in either of the first and second oral care implements, the head is non-detachable from the handle.

Optionally, in either of the first and second oral care implements, the oral care agent is selected from the group consisting of: antibacterial agents; oxidative or whitening agents; enamel strengthening or repair agents; tooth erosion preventing agents; tooth anti-sensitivity ingredients; gum health actives; nutritional ingredients; tartar control or anti-stain ingredients; enzymes; sensate ingredients; flavors or flavor ingredients; breath freshening ingredients; oral malodor reducing agents; anti-attachment agents or sealants; diagnostic solutions; occluding agents, dry mouth relief ingredients; catalysts to enhance the activity of any of these agents; colorants or aesthetic ingredients; and combinations thereof. Further optionally, the oral care agent is selected from the group consisting of: antibacterial agents; oxidative or whitening agents; enamel strengthening or repair agents; tooth erosion preventing agents; tooth anti-sensitivity ingredients; gum health actives; nutritional ingredients; tartar control or anti-stain ingredients; enzymes; sensate ingredients; breath freshening ingredients; oral malodor reducing agents; diagnostic solutions; catalysts to enhance the activity of any of these agents; and combinations thereof.

Optionally, in either of the first and second oral care implements, the oral care implement is a toothbrush.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

In the following description, each of the exemplary embodiments of the oral care implement of the invention comprises a manually-operated oral care implement, more specifically a manually-operated toothbrush. However, in variations to these embodiments, the oral care implement could instead comprise a powered oral care implement, such as a powered toothbrush, wherein one or more oral care elements provided to the head of the implement are drivable so as to be moved relative to the handle of the implement. In still further embodiments, the oral care implement could instead comprise other forms of oral care implement, such as a soft-tissue cleaner, a tooth polisher, an interdental brush, a tongue scraper, or another implement designed for oral care. It is to be understood that other embodiments may be utilised, and that structural and functional modifications may be made without departing from the scope of the present invention.

Figure 1:
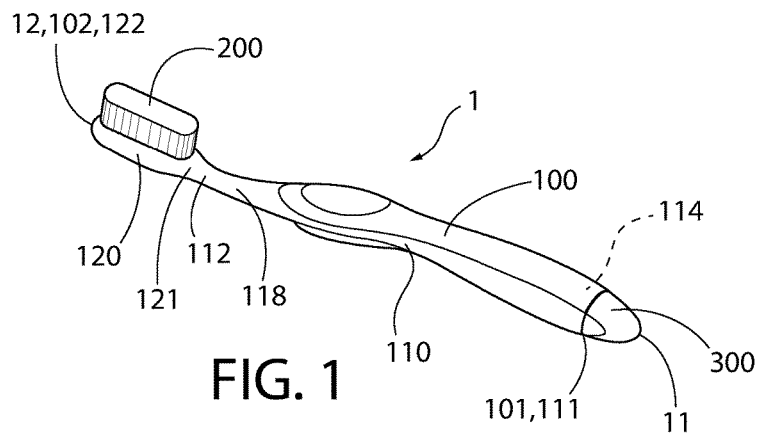
FIG. 1 shows a perspective view of an oral care implement according to an exemplary embodiment of the present invention, wherein a cap of the implement is at a first position relative to a body of the implement with an applicator of the implement in a storage state.
Figure 2:
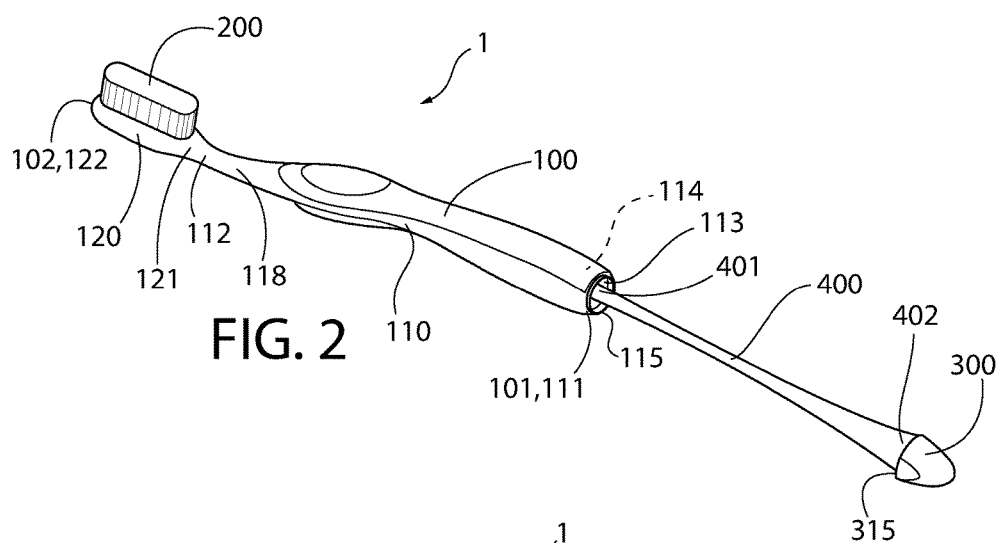
FIG. 2 shows a perspective view of the oral care implement of FIG. 1, wherein the cap is at a second position relative to a body with the applicator in an application state.
Figure 3:
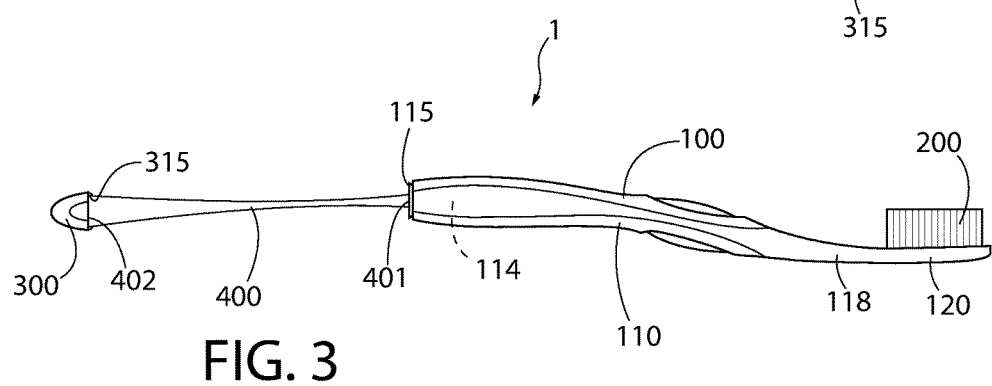
FIG. 3 shows a side profile view of the oral care implement of FIG. 2.

FIGS. 1 to 3 illustrate an oral care implement, in this case a toothbrush, according to an exemplary embodiment of the present invention, generally designated with the reference numeral 1. The toothbrush 1 generally comprises a body 100, oral care elements 200 on a head 120 of the body 100, a cap 300 at a proximal end 101 of the body 100, and an applicator 400 holding an oral care agent, each of which is described in more detail below.

The body 100 of the toothbrush 1 has the proximal end 101 and a distal end 102 and is elongate between the proximal and distal ends 101, 102. The body 100 comprises a handle 110 and a head 120 at a distal end 112 of the handle 110. The head 120 is a distal portion of the body 100 and has a proximal end 121 and a distal end 122, which distal end 122 forms the distal end 102 of the body 100. The head 120 has extending therefrom oral care elements 200 for cleaning or polishing surfaces in a user's mouth, such as surfaces of their teeth. In FIGS. 1 to 3, the oral care elements 200 are illustrated as a simple block for clarity. However, it will be appreciated that, in reality, the oral care elements 200 comprise a plurality of individually identifiable oral care elements.

The oral care elements 200 extend from a first, front side of the toothbrush 1 and are for cleaning or polishing surfaces in a user's mouth, such as surfaces of their teeth. As used herein, the term "oral care element" is used in a generic sense to refer to any structure that can be used to clean, massage or polish an oral surface, such as teeth or soft tissue, through relative surface contact. In this embodiment, the oral care elements comprise a plurality of tooth cleaning elements, preferably a plurality of flexible, nylon bristles arranged in tufts. However, in variations to this embodiment, the oral care elements may additionally or alternatively comprise one or more tooth polishing elements, preferably in the form of elastomeric tooth polishing elements, such as elastomeric protrusions, elements, fingers, or prophylactic (prophy) cups. In some embodiments, the oral car elements 200 may comprise at least one of any one or more of the following, without limitation: bristles, rigid bristles, flexible bristles, filament bristles, fibre bristles, nylon bristles, spiral bristles, rubber bristles, elastomeric protrusions, elastomeric elements, flexible polymer protrusions, co-extruded filaments, flag bristles, crimped bristles, anti-bacterial bristles and combinations thereof and/or structures containing such materials or combinations.

In a variation to the illustrated embodiment, a soft tissue cleaner may be provided on a second side of the toothbrush 1, such as a rear side of the toothbrush 1 opposite to the front side of the toothbrush 1. Such a soft tissue cleaner may be provided on an opposite side of the head 120 from the at least one oral care element 200.

The handle 110 is a proximal portion of the body 100 and has the distal end 112 and a proximal end 111, which proximal end 111 forms the proximal end 101 of the body 100. The handle 110 includes a neck portion 118 by which the handle 110 is connected with the head 120. The neck portion 118 is generally of a smaller cross sectional area than the rest of the handle 110. The neck portion 118 includes the distal end 112 of the handle 110, which is that portion of the handle 110 fixed to and closest to the proximal end 121 of the head 120. In the illustrated embodiment, the head 120 is non-detachable from the handle 110. However, in variations to the illustrated embodiment, the head 120 may be detachable from the handle 110, such as for replacement of the head 110 when the oral care elements 200 become worn.

The handle 110 provides a user with a mechanism by which he/she can readily grip and manipulate the toothbrush 1, includes ergonomic features which provide a high degree of control for the user while maintaining comfort, and may be formed of many different shapes and with a variety of constructions. Although the handle 110 is a non-linear structure in the illustrated embodiment, the invention is not so limited, and in certain embodiments the toothbrush 1 may have a simple linear handle 110.

A cavity 114 is provided in the handle 110 of the body 100 and the handle 110 defines an opening 113 of the cavity 114 at the proximal end 111 of the handle 110. In the illustrated embodiment, the opening 113 is the only access path into the cavity 114 from an exterior of the toothbrush 1.

The cap 300 of the toothbrush 1 is non-unitary with the body 100 and is usable for blocking the opening 113 defined by the body 100. In FIG. 1, the cap 300 is at a first position relative to the body 100. In the illustrated embodiment, when the cap 300 is at the first position relative to the body 100, the cap 300 is in contact with the body 100 so that a distance between the cap 300 and the body 100 is zero centimeters. Moreover, in the illustrated embodiment, when the cap 300 is at the first position relative to the body 100, a proximal end 11 of the toothbrush 1 is defined by the cap 300 and a distal end 12 of the toothbrush 1 is the distal end 102 of the body 100.

The body 100 and the cap 300 comprise respective co-operable couplers 115, 315 for coupling the cap 300 to the body 100 when the cap 300 is at the first position relative to the body 100. More specifically, in the illustrated embodiment, the respective co-operable couplers 115, 315 comprise a protrusion 115 protruding radially outwardly from the proximal end 101 of the body 100 and a depression 315 within the cap 300. The cap 300 is couplable to the body 100 by pressing the cap 300 in the direction of the body 100 with the protrusion 115 aligned with the depression 315, and the protrusion "snaps" into the depression 315. The cap 300 is decoupleable from the body 100 by pulling the cap 300 in a direction away from the body 100 with sufficient, yet small, force to "pop" the protrusion 115 out from the depression 315. In some variations to the illustrated embodiment, the respective co-operable couplers comprise a protrusion protruding radially outwardly from the cap 300 and a depression within the proximal end 101 of the body 100. In other variations to the illustrated embodiment, the respective co-operable couplers comprise respective co-operable threads on respective surfaces of the body 100 and the cap 300. Other suitable co-operable couplers for use in embodiments of the present invention will be apparent to the skilled person.

The cap 300 is movable relative to the body 100 between the first position (see FIG. 1) and a second position (see FIGS. 2 and 3). When the cap 300 is at the second position relative to the body 100, the cap 300 is at a second distance from the body 100, which second distance is greater than the first distance. The significance of this feature will become apparent on consideration of the following further features of the illustrated embodiment.

The applicator 400 of the toothbrush 1 is connected between the body 100 and the cap 300. Specifically, the applicator 400 has a first end 401 fixed to the body 100, more specifically fixed to a wall of the body 100 that defines the cavity 114, so that the first end 401 of the applicator 400 is at a fixed position relative to the body 100. The applicator 400 also has a second end 402 fixed to the cap 300, more specifically fixed to an inner wall of the cap 300, so that the second end 402 of the applicator 400 is at a fixed position relative to the cap 300. The first and second ends 401, 402 of the applicator 400 are non-detachable from the body 100 and the cap 300, respectively. The applicator 400 of the toothbrush 1 is elastic and stretchable. A length of the applicator 400, which is a distance between the first and second ends 401, 402 of the applicator 400, is dependent on the position of the cap 300 relative to the body 100. The applicator 400 has a first length when the cap 300 is at the first position relative to the body 100, as shown in FIG. 1, and the applicator 400 has a second length, greater than the first length of the applicator 400, when the cap 300 is at the second position relative to the body 100, as shown in FIGS. 2 and 3. The second length of the applicator 400 preferably is at least 200% the first length of the applicator 400, more preferably is at least 300% the first length of the applicator 400, and most preferably is at least 400% the first length of the applicator 400.

As will be readily apparent from consideration of FIGS. 2 and 3, in the illustrated embodiment, when the cap 300 is at the second position relative to the body 100, the cap 300 is connected to the body 100 only via, or by, the applicator 400. That is, when the cap 300 is at the second position relative to the body 100, the coupler 115 of the body 100 is uncoupled from the coupler 315 of the cap 300, and the cap 300 is out of contact with the body 100.

The applicator 400 holds one or more oral care agents, which may be oral care fluids. The oral care agent may be in any form such as a solid or a flowable material including, without limitation, a powder, a viscous pastes or gel, or a liquid. Preferably, the oral care agent is a flowable material. Any suitable oral care agent can be used in the present invention. For example, the oral care agent may be a whitening agent, including, without limitation, a peroxide containing tooth whitening composition.

In the illustrated embodiment, the oral care agent held by the applicator 400 is a whitening agent. However, in variations to the illustrated embodiment, the oral care agent is selected from the group consisting of: antibacterial agents; oxidative or whitening agents; enamel strengthening or repair agents; tooth erosion preventing agents; tooth anti-sensitivity ingredients; gum health actives; nutritional ingredients; tartar control or anti-stain ingredients; enzymes; sensate ingredients; flavors or flavor ingredients; breath freshening ingredients; oral malodor reducing agents; anti-attachment agents or sealants; diagnostic solutions; occluding agents, dry mouth relief ingredients; catalysts to enhance the activity of any of these agents; colorants or aesthetic ingredients; and combinations thereof. Preferably, the oral care agent is selected from the group consisting of: antibacterial agents; oxidative or whitening agents; enamel strengthening or repair agents; tooth erosion preventing agents; tooth anti-sensitivity ingredients; gum health actives; nutritional ingredients; tartar control or anti-stain ingredients; enzymes; sensate ingredients; breath freshening ingredients; oral malodor reducing agents; diagnostic solutions; catalysts to enhance the activity of any of these agents; and combinations thereof. In some embodiments, the applicator 400 holds more than one of the oral care agents listed in the preceding sentence.

The oral care agent preferably is free of (i.e., is not) toothpaste. Preferably, the oral care agent is intended to provide supplemental oral care benefits in addition to merely brushing one's teeth. Other suitable oral care agents could include lip balm or other materials that are typically available in a semi-solid state.

In the illustrated embodiment, the applicator 400 is porous or absorbent and the applicator 400 holds the oral care agent in the pores of the applicator 400, as well as on a surface of the applicator 400. In variations to the illustrated embodiment, the applicator 400 may not be porous or absorbent. In some such variations to the illustrated embodiment, the applicator 400 holds the oral care agent only on the surface of the applicator 400. For example, in some embodiments of the invention, the surface of the applicator 400 is textured for holding the oral care agent. The surface of the applicator may include a plurality of dimples, cups or recesses, similar to the dimples on a golf ball, within which the oral care agent is held. The oral care agent may be held on the surface of the applicator 400 through the provision of a specific relationship between a surface tension of the oral care agent and the dimensions of the dimples, cups or recesses. Other mechanisms by which the oral care agent may be held by the applicator 400 will be apparent to the skilled person in light of the full disclosure.

As discussed above, the cap 300 is movable relative to the body 100 between the first position and the second position. When the cap 300 is at the first position relative to the body 100, as shown in FIG. 1, the applicator 400 is in a storage state located in the cavity 114 and the cap 300 blocks the opening 113. More specifically, in the illustrated embodiment, the cap 300 seals the opening 113, and the body 100 and the cap 300 co-operate to isolate the cavity 114, the applicator 400 and the oral care agent(s) held by the applicator 400 from the exterior of the toothbrush 1. Accordingly, the oral care implement 1 is compact, and the oral care agent(s) held by the applicator 400 are well preserved, when the applicator 400 is in the storage state.

In a variation to the illustrated embodiment, a resilient seal, such as an O-ring, may be provided on the body 100 or on the cap 300, which resilient seal is located around the opening 130 and compressed between the body 100 and the cap 300, when the cap 300 is at the first position relative to the body 100, thereby to better ensure that the cavity 114, the applicator 400 and the oral care agent(s) held by the applicator 400 are isolated from the exterior of the toothbrush 1. Preferably, the resilient seal makes the cavity 114 water-tight and/or air-tight. The resilient seal may be partially molded into the material of the body 100 or cap 300, respectively, or may be attached thereto, such as by an adhesive, during manufacture of the toothbrush 1.

When a user wishes to use the applicator 400, they move the cap 300 relative to the body 100 from the first position towards the second position shown in FIGS. 2 and 3. More specifically, they first decouple the cap 300 from the body 100 by pulling the cap 300 in a direction away from the body 100 with sufficient force to decouple the protrusion 115 from the depression 315, and then they continue to move the cap 300 relative to the body 100 towards the second position, so that the applicator 400 becomes stretched between the body 100 and the cap 300 and is placed in fluid communication with the exterior of the toothbrush 1. When the cap 300 reaches the second position relative to the body 100, the applicator 400 is exposed in an application state. When the cap 300 is at the second position relative to the body 100, the applicator 400 extends from within the cavity 114 through the opening 113. In the illustrated embodiment, when the cap 300 is at the second position relative to the body 100, the distance (the "second distance") between cap 300 and the body 100 is between 5 and 15 centimeters, more preferably between 8 and 15 centimeters, and most preferably between 10 and 15 centimeters. Accordingly, a typical user is able to rub the applicator 400 on their teeth and/or gums and/or tongue, in order to apply the oral care agent(s) held by the applicator 400 onto their teeth and/or gums and/or tongue. After applying the oral care agent(s) held by the applicator 400 onto their oral surface(s), the user then moves the cap 300 relative to the body 100 from the second position to the first position, to allow the applicator 400 to contract and retract into the cavity 114, and couples the cap 300 to the body 100 by pressing the cap 300 in the direction of the body 100 with the protrusion 115 aligned with the depression 315, so that the protrusion "snaps" into the depression 315 and so that the applicator 400 is placed back in the storage state.

Accordingly, the applicator of the toothbrush 1 is very convenient to use to apply an oral care agent to an oral surface. The implement 1 is reusable multiple times to apply the oral care agent to an oral surface.

In variations to the illustrated embodiment, the cavity 114 may be provided elsewhere in the body 100 than at the position shown in the Figures. For example, the cavity 114 may be provided in the handle 110 away from the proximal end 111 of the handle 110, such as in or adjacent to the neck portion 118 of the handle 110. In some variations to the illustrated embodiment, the handle 110 may define an opening 113 of the cavity 114 away from the proximal end 111 of the handle 110, such as in or adjacent to the neck portion 118 of the handle 110 or at the distal end 112 of the handle 110. In some variations to the illustrated embodiment, the cavity may be in the head 120 of the body 100 and the head 120 may define an opening of the cavity. In some variations to the illustrated embodiment, the cavity may be in both the handle 110 and the head 120 of the body 100. An opening into such a cavity in both the handle 110 and the head 120 may be defined by the handle 110 or by the head 120. In some embodiments, a plurality of cavities may be provided in the body 100, and respective openings of the cavities may be defined by the handle 110 and/or by the head 120.

In variations to the illustrated embodiment, the cavity 114 may be provided in the cap 300 instead of in the body 100. In such variations, the cap 300 would define the opening of the cavity, and the body 100 could block the opening when the cap 300 is at the first position relative to the body 100.

In some variations to the illustrated embodiment, the cap 300 may be unitary with the body 100. For example, the cap 300 may be connected to the body 100 by a living hinge. Nevertheless, the cap 300 still may be usable for blocking the opening 113 defined by the body 100, and the cap 300 would still be movable relative to the body 100 from a first position to a second position to change the state of the applicator 400 from a storage state to an application state.

What is claimed is:

1. An oral care implement, comprising:
   a body comprising a handle and a head at an end of the handle, the head having at least one oral care element extending therefrom;
   a cap movable relative to the body;
   a cavity in one of the body and the cap, the one of the body and the cap defining an opening of the cavity; and
   an applicator connected between the body and the cap and holding an oral care agent;
   wherein the cap is movable relative to the body between a first position, at which the cap is at a first distance from the body, and a second position, at which the cap is at a second distance from the body, wherein the second distance is greater than the first distance; and
   wherein the cap is connected to the body only via the applicator when the cap is at the second position relative to the body.

2. The oral care implement of claim 1, wherein the applicator is located in the cavity and the other of the body and the cap blocks the opening when the cap is at the first position relative to the body, and wherein the applicator is in fluid communication with an exterior of the oral care implement when the cap is at the second position relative to the body.

3. The oral care implement of claim 1, wherein the cavity is in the handle.

4. The oral care implement of claim 3, wherein the handle has a proximal end and a distal end, wherein the head is at the distal end of the handle, and wherein the opening is at the proximal end of the handle.

5. The oral care implement of claim 1, wherein the cap is in contact with the body when the cap is at the first position relative to the body.

6. The oral care implement of claim 1, wherein the cap is non-unitary with the body.

7. The oral care implement of claim 1, wherein the body and the cap comprise respective co-operable couplers for coupling the cap to the body when the cap is at the first position relative to the body, and wherein the respective co-operable couplers comprise a protrusion from one of the body and the cap and a depression in the other of the body and the cap.

8. The oral care implement of claim 1, wherein the applicator is porous.

9. The oral care implement of claim 1, wherein the applicator is non-detachable from one or both of the body and the cap.

10. The oral care implement of claim 1, wherein the applicator is elastic.

11. The oral care implement of claim 1, wherein the applicator is stretchable.

12. The oral care implement of claim 1, wherein a first end of the applicator is at a fixed position relative to the body and/or wherein a second end of the applicator is at a fixed position relative to the cap.

13. The oral care implement of claim 1, wherein the head is non-detachable from the handle.

14. The oral care implement of claim 1, wherein the oral care agent is selected from the group consisting of: antibacterial agents; oxidative or whitening agents; enamel strengthening or repair agents; tooth erosion preventing agents; tooth anti-sensitivity ingredients; gum health actives; nutritional ingredients; tartar control or anti-stain ingredients; enzymes; sensate ingredients; flavors or flavor ingredients; breath freshening ingredients; oral malodor reducing agents; anti-attachment agents or sealants; diagnostic solutions; occluding agents, dry mouth relief ingredients; catalysts to enhance the activity of any of these agents; colorants or aesthetic ingredients; and combinations thereof; further optionally wherein the oral care agent is selected from the group consisting of: antibacterial agents; oxidative or whitening agents; enamel strengthening or repair agents; tooth erosion preventing agents; tooth anti-sensitivity ingredients; gum health actives; nutritional ingredients; tartar control or anti-stain ingredients; enzymes; sensate ingredients; breath freshening ingredients; oral malodor reducing agents; diagnostic solutions; catalysts to enhance the activity of any of these agents; and combinations thereof.

15. The oral care implement of claim 1, wherein the oral care implement is a toothbrush.

16. An oral care implement, comprising:
a body comprising a handle and a head at an end of the handle, the head having at least one oral care element extending therefrom;
a cap movable relative to the body;
a cavity in one of the body and the cap, the one of the body and the cap defining an opening of the cavity; and
an applicator connected between the body and the cap and holding an oral care agent;
wherein the cap is movable relative to the body between a first position, at which the applicator is located in the cavity and the other of the body and the cap blocks the opening, and a second position, at which the applicator is in fluid communication with an exterior of the oral care implement; and
wherein the applicator is non-detachable from one or both of the body and the cap.

17. The oral care implement of claim 16, wherein the cap is at a first distance from the body when the cap is at the first position relative to the body, wherein the cap is at a second distance from the body when the cap is at the second position relative to the body, and wherein the second distance is greater than the first distance.

18. The oral care implement of claim 16, wherein the cap is connected to the body only via the applicator when the cap is at the second position relative to the body.

19. An oral care implement comprising:
a body comprising a handle and a head at an end of the handle, the head having at least one oral care element extending therefrom;
a cap movable relative to the body;
a cavity in one of the body and the cap, the one of the body and the cap defining an opening of the cavity; and
an applicator connected between the body and the cap and holding an oral care agent;
wherein the cap is movable relative to the body between a first position, at which the cap is at a first distance from the body, and a second position, at which the cap is at a second distance from the body, wherein the second distance is greater than the first distance; and
wherein a length of the applicator is dependent on a position of the cap relative to the body.

20. The oral care implement of claim 19, wherein the applicator has a first length when the cap is at the first position relative to the body, wherein the applicator has a second length when the cap is at the second position relative to the body, and wherein the second length is greater than the first length.

* * * * *